United States Patent [19]
Takano et al.

[11] Patent Number: 5,932,781
[45] Date of Patent: Aug. 3, 1999

[54] ECTOINE SYNTHASE GENE

[75] Inventors: Mitsuo Takano, Toyonaka; Hisayo Ono, Takatsuki; Hiroyuki Yamada, Osaka; Kazuhiko Yamatoya, Izumisano, all of Japan

[73] Assignee: Dainippon Pharmaceutical Co., Ltd., Osaka, Japan

[21] Appl. No.: 08/640,978

[22] PCT Filed: Nov. 1, 1994

[86] PCT No.: PCT/JP94/01839

§ 371 Date: May 9, 1996

§ 102(e) Date: May 9, 1996

[87] PCT Pub. No.: WO95/13366

PCT Pub. Date: May 18, 1995

[30] Foreign Application Priority Data

Nov. 9, 1993 [JP] Japan ................................... 5-304768

[51] Int. Cl.$^6$ ........................... C12N 15/00; C12N 15/82; C12N 15/29; A01H 4/00
[52] U.S. Cl. ......................... 800/288; 800/298; 800/278; 800/288; 435/320.1; 435/419; 435/468; 536/236; 536/23.7; 536/24.1

[58] Field of Search ...................................... 800/205, 298, 800/278, 288; 435/172.3, 320.1, 419, 468; 536/23.6, 23.7, 24.1

[56] References Cited

PUBLICATIONS

Yamamoto et al., "Summary of Symposium of Japan Biotechnology Society," p. 203 (1992).

*Primary Examiner*—Lynette F. Smith
*Assistant Examiner*—Thomas Haas
*Attorney, Agent, or Firm*—Birch, Stewart, Kolasch & Birch, LLP

[57] ABSTRACT

The nucleotide sequence of a DNA coding for ectoine synthase has been determined by isolating a gene coding for an enzyme involved in the biosynthesis of ectoine in the form of a DNA comprising about 4.2 kilobase pairs which is obtained from Halomonas sp. KS-3 by cleaving with restriction endonucleases EcoRI and SalI. By introducing the obtained gene DNA into *E. coli,* it is possible to provide the capability of biosynthetizing ectoine and the characteristic of high osmotic tolerance, thus permitting the development of an efficient fermentation technique utilizing the resultant transformant and the creation of plants having high resistance to drought.

13 Claims, 1 Drawing Sheet

5,932,781

ECTOINE SYNTHASE GENE

TECHNICAL FIELD

This invention relates to a DNA coding for an enzyme involved in the biosynthesis of ectoine, a method for giving ectoine synthetic ability to a host cell by introducing said DNA thereto, and a transformed host cell.

PRIOR ART

Under an environment of a high osmotic pressure, a certain microorganisms can obtain a tolerance to the surrounding stress by accumulating so-called "compatible solute" within their cells. It is known that the compatible solute includes saccharides, polyols, betaines or a certain amino acids (cf. Truper, H. G. et al., Experientia, Vol. 42, pp. 1182–1187, 1986).

Ectoine is a cyclic amino acid, which is 1,4,5,6-tetrahydro-2-methyl-4-pyrimidinecarboxylic acid or 3,4,5,6-tetrahydro-2-methyl-4-pyrimidinecarboxylic acid. Said ectoine has been found as a compatible solute which is produced by a halophilic microorganism, *Ectothiorhodospira halochloris,* and it is further known that it has a tolerance to a high osmotic pressure ("high osmotic tolerance") [cf. Galinski, E. A. et al., Eur. J. Biochem., Vol. 149, pp. 135–139, 1985; Mitsuo Takano et al., a program for Symposium of The Japan Fermentation Engineering Association, p. 193, 1988]. There are also some reports as to the biosynthetic pathway of ectoine (cf. Peters, P. et al., FEMS Microbiol. Lett., Vol. 71, pp. 157–162, 1990) and as to the physical properties thereof (cf. Khunajakr, N., et al., Annual Reports of International Center of Cooperative Research in Biotechnology, Japan, Vol. 12, pp. 157–167, 1989).

Ectoine is biosynthetized from L-aspartate-$\beta$-semialdehyde, in which steps L-diaminobutyric acid transaminase, L-diaminobutyric acetyltransferase, and ectoine synthase are involved. Hereinafter, these enzymes are generally called as "ectoine synthetases". As a system being capable of inducing the biosynthesis of an enzyme by bacteria, there is known so-called "operon" which is a regulatory system for expression of a gene, where a series of enzymes are synchronously induced by a single regulatory gene. The ectoine synthase is an enzyme which can synthetize ectoine from a-N-acetyl-diaminobutyric acid, and there are reports concerning a method for isolating and purifying said enzyme from a halophilic microorganism and the properties thereof (cf. Mihoko Yamamoto, et al., Summary of Symposium of Japan Biotechnology Society, p. 203, 1992). However, the gene structure and nucleotide sequence of the ectoine synthase and the ectoine synthetases have never been known.

On the basis of a knowledge that a certain micro-organism can accumulate ectoine within the cells thereof and thereby can grow even under an environment condition of strong stress to living bodies (e.g. high osmotic pressure), it has been proposed a method for extracting and isolating ectoine by aiming at the function of ectoine (cf. Khunajakr, N. et al., Annual Reports of International Center of Cooperative Research in Biotechnology, Japan, Vol. 12, pp. 157–167, 1989) and a method for chemical synthesis of ectoine (cf. JP-A-3-31265).

DISCLOSURE OF THE INVENTION

Aiming at the specific function of the ectoine, the present inventors have intensively investigated the ectoine from the following viewpoints. Where a high osmotic tolerance is given to, for example, a microorganism or a plant by giving an ability of biosynthesis of ectoine, not to ectoine per se, it will be able to develop a method for the efficient production of an useful product by a fermentation in a high concentration, and further it will be able to create a plant having a resistance to drought and having tolerance to a high osmotic pressure due to the droughty circumstance. Moreover, where the microorganisms are grown in a droughty ground such as in a desert, it will be also possible to change to a fertilized soil and further to create a plant which is suitable for planting in a droughty ground and at highly salty environment such as at a seaside.

BEST MODE FOR CARRYING OUT THE INVENTION

Figure 1:
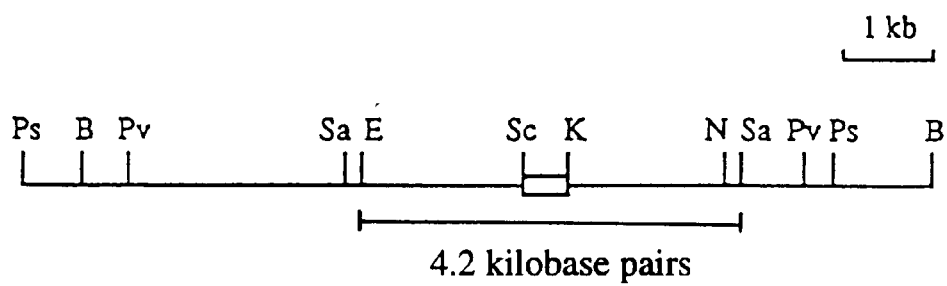
FIG. 1 shows a restriction endonuclease map of a DNA of a microorganism of the genus Halomonas, KS-3 strain, The signals in said figure mean the sites to be cleaved by each restriction endonuclease, respectively. Besides, the part of box means a region coding for ectoine synthase. Ps, PstI; B, BamHI; Pv, PvuII; Sa, SalI; E, EcoRI; Sc, ScaI; k, KpnI; n, NruI.

Aiming at the existence of bacteria which can grow under a highly salty environment and can accumulate ectoine within the cells and thereby can exhibit high tolerance to a high osmotic pressure, the present inventors have looked for and have collected a bacteria having such characteristics from a soil at a northeastern area in Tailand and identified it. The bacteria having a high osmotic tolerance is classified as a Gram negative, aerobic bacillus of the genus Halomonas, which is positive in catalase, GC of DNA: 65.4–65.7 mol.%, and grows in a concentration of sodium chloride of from 0.3% to 24% (cf. Mitsuyoshi Okuda, et al., Summary of Symposium of Halophilic Microorganisms Research Association, Vol. 25, pp. 14–17, 1988). This bacteria was designated as "Halomonas sp. KS-3" and deposited to National Institute of Bioscience and Human-Technology, Agency of Industrial Science and Technology under Budapest Treaty with an accession number of FERM BP-4841 (accepted on Oct. 20, 1994) which has originally been deposited as an accession number of FERP P-13952 (accepted on Nov. 5, 1993).

It has been confirmed by the inventors that the Halomonas sp. KS-3 strain can produce ectoine (in accordance with the method as described in Khunajakr, N. et al., Annual Reports of International Center of Cooperative Research in Biotechnology, Japan, Vol. 12, pp. 157–167, 1989) and then ectoine synthase has been isolated from said culture cells. That is, the culture cells are lyzed with lysozyme, and after removing the nucleic acid with protamine sulfate, the natural type ectoine synthase is isolated and purified by subjecting it to salting-out with ammonium sulfate, a hydrophobic column chromatography, and a hydroxyapatite column chromatography. It has a molecular weight of about 19 kilodalton (kDa) measured by electrophoresis with SDS-polyacrylamide gel, and further, it has an isoelectric point of 4.2–4.4. It has also been determined that it has an amino acid sequence having 30 amino acid residues from the N-terminus as shown in SEQ ID NO: 3 according to an amino acid sequencer (Applied Biosystems).

Moreover, the present inventors have succeeded to isolate a gene DNA coding for ectoine synthase from the gene DNA of Halomonas sp. KS-3 based on the above N-terminus amino acid sequence, and then determined the nucleotide sequence. The nucleotide sequence of the DNA coding for the ectoine synthase is shown in SEQ ID NO: 2.

The DNA coding for the ectoine synthase can be isolated by the following procedure. That is, the 4.2 kbp-DNA-EcoRI-SalI fragment is cleaved with restriction endonucleases MboI and NspBII to isolate a fragment having 228 base pairs of the nucleotide Nos. of from 3 to 230, and a fragment having 178 base pairs of the nucleotide Nos. of from 231 to 408 in the nucleotide sequence as shown in SEQ ID NO: 2, and the both fragments are ligated by T4 DNA ligase to give a DNA fragment having 406 base pairs of the nucleotide Nos. of from 3 to 408. Thereafter, the truncated both termini thereof are repaired by a DNA chemically synthesized to give the desired DNA coding for ectoine synthase. Alternatively, the 4.2 kbp-DNA-EcoRI-SalI fragment is cleaved with restriction endonucleases AspAII (another name: BstEII) and NspBII to isolate a fragment of the nucleotide Nos. of from 46 to 408, and then the truncated both termini thereof are repaired by a DNA chemically synthesized to give the desired DNA coding for ectoine synthase.

The whole amino acid sequence of the ectoine synthase is determined based on the nucleotide sequence, which is as shown in SEQ ID NO: 1. It was confirmed that the sequence of N-terminus amino acids is completely identical with that of the 30 N-terminus amino acids of the natural type ectoine synthase. The ectoine synthase is a protein which is composed of 137 amino acids and has a molecular weight of 15.5 kDa. The amino acid components are also well identical to the data determined (cf. Table 1) for the natural type ectoine synthase. The nucleotide sequence encoding the ectoine synthase as well as the corresponding amino acid sequence are shown in SEQ ID NO: 4.

TABLE 1

Amino acid components of ectoine synthase

| Amino acid | Natural type enzyme | Nucleotide sequence |
|---|---|---|
| Lys | 5 | 5 |
| His | 8–9 | 9 |
| Trp | ≧2 | 2 |
| Arg | 7 | 7 |
| Asp/Asn | 15–16 | 16 |
| Thr | 9–10 | 10 |
| Ser | 5 | 5 |
| Glu/Gln | 19 | 18 |
| Pro | 5 | 5 |
| Gly | 11 | 11 |
| Ala | 10 | 10 |
| Cys | >2 | 3 |
| Val | 6–7 | 6 |
| Met | 2 | 2 |
| Ile | 8–9 | 9 |
| Leu | 11 | 11 |
| Tyr | 4 | 4 |
| Phe | 4 | 4 |
| Total number | >133 | 137 |

The columns of the natural type enzyme and the nucleotide sequence in the above Table 1 mean the amino acid components of the natural type ectoine synthase and the amino acid components of the ectoine synthase which is determined based on the nucleotide sequence, respectively.

The present inventors have isolated the about 4.2 kbp DNA fragment obtained from Halomonas sp. KS-3 by cleaving by restriction endonucleases EcoRI and SalI. After confirming that the nucleotide sequence coding for the ectoine synthase as shown in SEQ ID NO: 2 is contained in this DNA fragment, it is inserted into plasmid pBR322 and introduced into E. coli, and then, it has been found that the transformed E. coli has the desired high osmotic tolerance so that it can grow even in a medium of a high salt concentration. Owing to the transformation the gene of enzyme effective for synthesis of ectoine exhibits its function, and thereby ectoine is synthetized and accumulated within the cells, as a result, E. coli has characteristics of high osmotic tolerance.

According to the present invention, the DNA coding for an enzyme effective for synthesis of ectoine is recombined to a vector replicable within host cells, followed by introducing it into a host, and thereby, the host is given by a capability of synthetizing efficiently ectoine and hence acquires characteristics of high osmotic tolerance. By utilizing this technique, there can be prepared micro-organisms and plants which have high osmotic tolerance, and hence, it will be possible to develop an efficient fermentation method using said transformant, creation of plants having high resistance to drought, and improvement of soil in desert.

The first object of the present invention is to provide a DNA coding for ectoine synthase. An example of a nucleotide sequence of the DNA coding for ectoine synthase is the sequence shown in SEQ ID NO: 2 and an allele thereof. The amino acid sequence of the ectoine synthase is shown in SEQ ID NO: 1. The amino acid sequence may partially be changed by modifications, deletions, additions, and the like in accordance with a genetic engineering technique. Such a modified enzyme is also included in the present invention as far as it has the essential enzymatic properties of ectoine synthase, and hence, the nucleotide sequence coding for the enzyme is also included in the present inventon. Based on the information of the amino acid sequence shown in SEQ ID NO: 1, a DNA coding for ectoine synthase can also be chemically synthetized by selecting the codons suitable for a host cell.

The second object of the invention is to provide a DNA fragment containing a gene coding for ectoine synthase. Specifically, it is a DNA comprising about 4.2 kilobase pairs which is obtained from Halomonas sp. KS-3 by cleaving with restriction endonucleases EcoRI and SalI and has the nucleotide sequence as shown in SEQ ID NO: 2.

The third object of the invention is to provide a recombinant DNA self-replicable within the host cells, which is prepared by recombining a DNA coding for ectoine synthase to a vector DNA self-replicable within the host cells.

The fourth object of the invention is to provide a method for providing an ability of biosynthesis of ectoine to a host cell, which comprising introducing a recombinant DNA containing a DNA coding for ectoine synthase into a host cell.

The fifth object of the invention is to provide microorganisms or plants which are transformed by introducing a recombinant DNA containing a DNA coding for ectoine synthase.

The DNA coding for ectoine synthase of the invention can be detected by determining the nucleotide sequence of the product and then comparing it with the nucleotide sequence as shown in SEQ ID NO: 2, or by southern blotting hybridization using as a probe a fragment of the DNA having a nucleotide sequence as shown in SEQ ID NO: 2, or by transforming E. coli by introducing the gene and confirming the growth thereof in a medium having a high salt concentration.

Determination of ectoine in cells: It is carried out by the steps of extracting the cells with a 10 times larger volume of a 70% ethanol at 80° C. for 10 minutes, filtering it with a glass filter to give a crude extract, removing ethanol from the crude extract by concentration under reduced pressure (at 35° C.), adding an equivolume of chloroform to the concentrated solution, centrifuging (1,500 rpm, 10 minutes), and again concentrating the supernatant under reduced pressure, diluting the concentrated solution with a distilled water, charging it onto a cation exchange column (DIAION SKLB, manufactured by Mitsubishi Chemical), washing it with water, eluting ectoine therefrom with 3N ammonium hydroxide, removing ammonium hydroxide from the eluate by concentrating under reduced pressure, and charging the resultant onto an anion exchange column (DIAION SA10A, manufactured by Mitsubishi Chemical) to isolate the ectoine. The analysis of ectoine can be carried out by high performance liquid chromatography or a thin layer chromatography in accordance with a method of Peters, P., et al. (cf. FEMS Microbiol. Lett., Vol. 71, pp. 157–162, 1990).

Determination of the enzyme activity of ectoine synthase: It is carried out by adding an enzyme to be tested to a reaction mixture consisting of 80 mM Tris-HCl buffer (pH 9.5), 4.4 mM α-N-acetyl-diaminobutyric acid, 0.77 M sodium chloride (the total volume of the reaction mixture: 45 μL), reacting at 15° C. for 10 minutes, quenching the reaction by adding thereto an equiamount of 0.6% trifluoroacetic acid, and analyzing the amount of the produced ectoine in the reaction mixture by high performance liquid chromatography. One unit of the enzyme activity of ectoine synthase is defined as an amount of the enzyme which can produce 1 μmole of ectoine per one minute.

In the present invention, the bacteria used for isolating the DNA coding for ectoine synthase is not limited to Halomonas sp. KS-3, but includes any microorganisms which are capable of producing ectoine. The known microorganisms are, for example, *Ectothiorhodospira halochloris* (American Type Culture Collection, accession number, ATCC 35916) (cf. Galinski, E. A. et al., Eur. J. Biochem., Vol. 149, pp. 135–139, 1985), *Halomonas elongata* (cf. Wohlfarth, A. et al., J. Gen. Microbiol., Vol. 136, pp. 705–712, 1990), Vibrio costicola (cf. Regev. R. et al., Arch. Biochem. Biophys., Vol. 278, pp. 106–112, 1990). The DNA coding for an enzyme involved in the biosynthesis of ectoine can be isolated from a bacteria of the genus Halomonas or any other cells, which may have the same or highly homologous nucleotide sequence, by hybridization method using as a probe a DNA having the nucleotide sequence as shown in SEQ ID NO: 2. Moreover, based on the information of the nucleotide sequence as shown in SEQ ID NO: 2 or of the amino acid sequence as shown in SEQ ID NO: 1, a DNA coding for ectoine synthase can also be chemically synthetized by selecting the codons suitable for a host cell. Furthermore, a DNA coding for ectoine synthase which has a modified structure may also be produced by partially modifying the DNA coding for ectoine synthase in accordance with a site-specific mutation method (cf. Kunkel, T. A. et al., Methods in Enzymol., Vol. 154, pp. 367–392, 1987).

The expression of a foreign gene within host cells can be done by the methods as described in many textbooks and literatures (for example, Molecular Cloning; A Laboratory Manual, 2nd Ed. Vol. 1–3, ed. by Sambrook, J. et al, Cold Spring Harbor Laboratory Press, New York 1989), and the basic theory thereof has already been established. A recombinant DNA being replicable and functioning in the host cells can be produced by adding a translation initiation codon at the upstream of a DNA coding for the desired protein to be expressed and a translation termination codon at the downstream thereof, adding regulatory genes such as a promoter sequence which can regulate the transcription (e.g. trp, lac, phoS, PL, SV40 early promoter), and inserting it into an appropriate vector (e.g. pHY300PLK, pBR322, pUC19, pYAC-neo). The expression vector has preferably genetic information for replicating within host cells and can replicate therein and has preferably a gene to be functioned as a detectable marker. The most suitable vector is selected depending on the kinds of hosts. Moreover, a suitable promoter functionable within the host cells is also chosen. A regulatory gene derived from the host cells is preferable from the viewpoint of exhibiting the desired functions.

Introduction of the gene into microorganisms (e.g. bacteria, yeast) and plants can be done by a calcium chloride method (e.g. Cohen, S. N. et al, Proc. Natl. Acad. Sci. USA, Vol. 69, pp. 2110–2114, 1972), a DEAE-dextran method (e. g. Current Protocols in Molecular Biology, Vol. 1, Chapter 9.2, ed. by Ausubel, F. M. et al, John Wiley & Sons, 1987), an electroporation method, a method using protoplast, a method using Ti plasmid, a method using a virus vector (e.g. Watson J. D. et al., Molecular Biology of Recombinant DNA, translated by Michio Matsuhashi et al., issued by Maruzen, 1993).

The basic procedures of genetic engineering technique shall be referred to many literatures and technical texts, for example, Molecular Cloning; A Laboratory Manual, 2nd. Ed., Vol. 1–3, by Sambrook, J. et al, Cold Spring Harbor Laboratory Press, New York 1989; Current Protocols in Molecular Biology, Vol. 1–2, by Ausubel, F. M. et al, Current Protocols, 1993; and Watson J. D. et al., Molecular Biology of Recombinant DNA, translated by Michio Matsuhashi et al., issued by Maruzen, 1993. The various instruments, enzymes and agents used in the technical field of this invention are used in the manner along with each guidance, reference note and manual.

The following abbreviations are used in order to simplify the description.

A: Adenine
C: Cytosine
G: Guanine
T: Thymine
Ala: Alanine
Arg: Arginine
Asn: Asparagine
Asp: Aspartic acid
Cys: Cysteine
Gln: Glutamine
Glu: Glutamic acid
Gly: Glycine
His: Histidine
Ile: Isoleucine
Leu: Leucine
Lys: Lysine
Met: Methionine
Phe: Phenylalanine Pro: Proline
Ser: Serine
Thr: Threonine
Trp: Tryptophan
Tyr: Tyrosine
Val: Valine
DNA: Deoxyribonucleic acid
kDa: kilodalton

EXAMPLES

The present invention is illustrated in more detail by referring to the following examples, but it should not be construed to be limited thereto and the present invention includes any modification by a conventional technique in the technical field of this invention.

Example 1

Isolation of a gene DNA of a bacteria of the genus Halomonas:

Halomonas sp. KS-3 was inoculated to a M63 medium (components: 1.4% $KH_2PO_4$, 0.4% KOH, 0.2% $(NH_4)_2SO_4$, 1 mM $MgSO_4$, 3.9 μM $FeSO_4$, 0.4% glucose) and thereto were added 3% sodium chloride and 0.25% yeast extract, and the mixture was aerobically pre-cultured at 37° C. overnight. This pre-culture broth was inoculated to a fresh M63 medium (100 ml) containing 3% sodium chloride in a concentration of 2% and it was aerobically cultured with shaking (140 rpm) at 37° C. After culturing for about 5 hours, when the culture broth had a turbidity of about 2 (absorbance at a wavelength of 660 nm), sodium chloride was added so as to be a final concentration of about 15%, and the mixture was further cultured for 5 hours. The cells were separated by centrifuge and washed to give cells (about 0.25 g).

A DNA was isolated from the cells by a conventional method (cf. Current Protocols in Molecular Genetics, ed. by Ausubel F. M. et al., p. 431, Cold Spring Harbor Laboratory Press, New York, 1972). That is, the cells were lyzed with protease K, centrifuged (8,000 rpm, for 10 minutes) to remove the residues, and then treated with ribonuclease. Thereafter, protein was removed by extracting with a mixture of an equiamount of phenol/chloroform, and then subjected to precipitation with ethanol to give the desired gene DNA of Halomonas bacteria (about 0.8 mg).

Example 2

Isolation of a DNA coding for ectoine synthase:

There were chemically synthetized two kinds of DNAs having 25 nucleotides which coded the amino acid sequences corresponding to both termini of the N-terminus amino acid sequences of the ectoine synthase as shown in SEQ ID NO: 3. The nucleotide sequences had the following formulae [I] and [II], respectively.

5'-TGATHGTNMGNAAYYTNGARGARGC-3'    [I]

5'-GNTYNSWNTYNGMNCANSWYAGGGT-3'    [II]

In the above formulae [I] and [II], M is either A or C, R is either A or G, W is either A or T, S is either G or C, Y is either C or T, H is either A or C or T, N is either A or G or C or T.

By using the chemically synthetized DNAs having the above formulae [I] and [II] as a primer, and also using the gene DNA of Halomonas bacteria obtained in Example 1 as a template, the desired gene DNA was specifically amplified by polymerase chain reaction with Ampli Taq Polymerase (manufactured by Perkin-Elmer Company) in accordance with the specification attached thereto. The temperature for modification, annealing and polymerase reaction were 95° C., 45° C., and 72° C., respectively.

The reaction product was subjected to an electrophoresis with a low melting agarose gel and then extraction to isolate the desired DNA fragment having 90 base pairs. This DNA fragment was inserted into plasmid pUC19 at the cleavage site with a restriction enzyme SmaI. The recombinant plasmid was introduced into E. coli DH5αF' (manufactured by Life Technologis, Inc.) to prepare a transformant. A recombinant plasmid was recovered from the transformant thus obtained, and the nucleotide sequence of the recombined DNA fragment having 90 base pairs was determined by dideoxy method. The amino acid sequence coded by the nucleotide sequence was completely identical to the sequence shown in SEQ ID NO: 3, by which it was confirmed to be the desired DNA fragment.

Example 3

Isolation of the gene DNA containing a DNA coding for ectoine synthase:

The gene DNA of Halomonas bacteria obtained in Example 1 was cleaved by 8 kinds of restriction endonucleases as mentioned below, and the fragments were isolated by an electrophoresis using an agarose gel. The used restriction endonucleases were EcoRI, SalI, ScaI, KpnI, BanHI, PvuII, NruI, and PstI. After isolating by the electrophoresis using an agarose gel, each DNA fragment was subjected to detection by southern blotting hybridization using as a probe a DNA fragement coding for ectoine synthase. As a result, a DNA containing completely the DNA coding for ectoine synthase, i.e. a DNA of about 4.2 kbp in size cleaved with EcoRI and SalI (this fragment is designated as "4.2 kbp-DNA-EcoRI-SalI fragment") was isolated. The result of analysis of the gene DNA of Halomonas bacteria with restriction endonucleases is shown in the accompanying FIG. 1.

Separately, there was isolated a large DNA fragment containing replication origin, ampicillin resistant gene, etc., which was obtained by cleaving plasmid pBR322 with EcoRI and SalI, (this fragment was designated as "pBR322-EcoRI-SalI fragment"). The 4.2 kbp-DNA-EcoRI-SalI fragment and the pBR322-EcoRI-SalI fragment were ligated with T4 DNA ligase to prepare a cyclic recombinant plasmid DNA. This recombinant DNA was designated as "pECT101".

Example 4

Nucleotide sequence of a DNA coding for ectoine synthase:

For the purpose of determining the nucleotide sequence of the 4.2 kbp-DNA-EcoRI-SalI fragment prepared in Example 3, it was inserted into the cloning region of a vector pBluescript II SK+ (manufactured by Toyobo Co., Ltd.) (this was designated as "pECT201"), and the nucleotide sequence was determined by using pBluescript II Exo/Mung DNA Sequencing System (manufactured by Stratagene Inc.). The nucleotide sequence coding for ectoine synthase and whole amino acid sequence are shown in SEQ ID NOS: 4 and 5.

EXAMPLE 5

Transformation with the DNA coding for ectoine synthase:

The recombinant DNA (pECT101) obtained in Example 3, which has been recombined with the 4.2 kbp-DNA-EcoRI-SalI fragment containing completely the DNA coding for ectoine synthase, was introduced into *E. coli* DH5αF' in accordance with the method described in Molecular Cloning; A Laboratory Manual, 2nd Ed., Vol. 1, 1.77–1.81 (ed. by Sambrook, J. et al., Cold Spring Harbor Laboratory Press, New York, 1989) to give a transformant having ampicillin resistance (it was designated as "*E. coli* DH5/pECT101"). Moreover, the transformant was subjected to hybridization, by which it was confirmed that the transformant contained a DNA coding for ectoine synthase.

Figure 2:
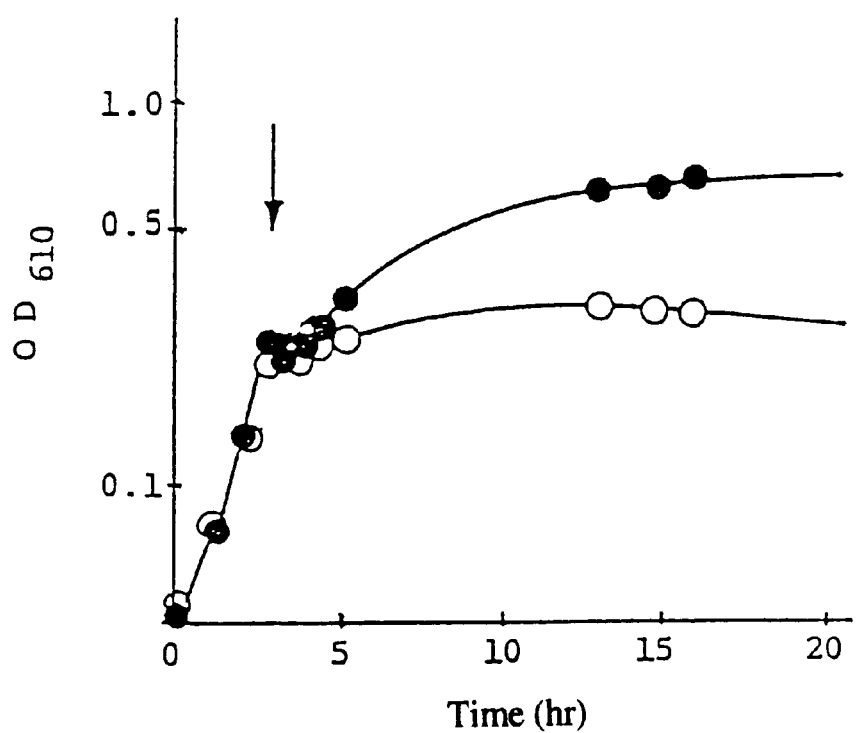
FIG. 2 shows the state of growing of trans-formants *E. coli* DH5/pECT101 and *E. coli* DH5/pBR322 in a medium having a high salt concentration, wherein the abscissa axis means the time for culture (hr.), the ordinate axis means the turbidity of the medium (absorbance at a wavelength of 610 nm), the arrow signal means the point when soidum chloride was added in a final concentration of 5%, and -O-: *E. coli* DH5/pECT101; -o-: *E. coli* DH5/pBR322.

The transformant *E. coli* DH5/pECT101 was inoculated to a M63 medium incorporated with 0.02% casamic acid and 2 μg/ml thyamine, and cultured at 37° C. When the turbidity of the culture broth (the absorbance at a wavelength of 610 nm) became about 0.2, sodium chloride was added so as to be a final concentration of 5%, and the culture was continued, where the growth state of the bacteria was observed with Bioscanner OT-BS-48 (manufactured by Ohtake Seisakusho). Plasmid pBR322 was introduced into *E. coli* DH5αF' likewise to give a transformant having ampicillin resistance (it was designated as "*E. coli* DH5/pBR322"), which was used as a reference transformant. As a result, as is shown in the accompanying FIG. 2, the reference transformant (*E. coli* DH5/pBR322) discontinued to grow in a medium having a high salt concentration. On the contrary, the transformant *E. coli* DH5/pECT101 grew well even in a medium having a high salt concentration. This means that the product of the invention acquired such characteristics as being capable of growing even under the environmental condition of a high salt concentration as well as the high osmotic pressure environment induced by the high salt concentration because of giving an ability of synthesis of ectoine by the introduction of a gene of ectoine synthase, and thereby having high tolerance to such environmental conditions.

UTILIZATION IN INDUSTRIES

By a genetic engineering technology using the gene DNA of ectoine synthase of the present invention, there can be produced ectoine which may be useful as a water-retaining material. Besides, when the DNA of the present invention is recombined into various microorganisms and plants by using an appropriate expression vector, there can be expressed a product having characteristics of being tolerant even under environmental conditions of a high osmotic pressure, and thereby, the process for cultivation of microorganisms may be improved so as to be able to proceed even in a high concentration and further there can be obtained plants having high resistance to drought and also tolerance to high osmotic pressure. This will be effective for revival of micro-organisms in soil of desert, and further creation of plants which can grow even in a droughty ground or at a seaside.

---

What is claimed is:

1. An isolated DNA coding for ectoine synthase.

2. A DNA as claimed in claim 1, which is a DNA coding for ectoine synthase having an amino acid sequence shown in SEQ ID NO: 1 or an allelic variant thereof.

3. A DNA as claimed in claim 1 or claim 2, wherein the DNA coding for ectoine synthase has a nucleotide sequence as shown in SEQ ID NO: 2.

4. A DNA comprising about 4.2 kb base pairs which is obtained from a bacteria of the genus Halomonas by cleaving the DNA of said bacteria with restriction endonucleases EcoRI and SaII and wherein said DNA contains a nucleic acid sequence coding for ectoine synthase.

5. A recombinant DNA which comprises the DNA as set forth in claim 1 which is recombined into a vector being replicable within a host cell.

6. A method for providing an ability of biosynthesis of ectoine to a host cell, which comprises introducing a recombinant DNA as set forth in claim 5 into the host cell.

7. A microorganism which is transformed with the recombinant DNA as set forth in claim 5.

8. A plant which is transformed with the DNA as set forth in claim 5.

9. A recombinant DNA which comprises the DNA as set forth in claim 2 which is recombined into a vector being replicable within a host cell.

10. A recombinant DNA which comprises the DNA as set forth in claim 3 which is recombined into a vector being replicable within a host cell.

11. A recombinant DNA which comprises the DNA as set forth in claim 4 which is recombined into a vector being replicable within a host cell.

12. An isolated bacterial DNA coding for ectoine synthase.

13. The DNA of claim 12, wherein said bacterial source of said DNA is selected from the group consisting of *Ectothiorhodospira halochloris, Halomonas elongata,* and *Vibrio consticola.*

* * * * *

UNITED STATES PATENT AND TRADEMARK OFFICE
CERTIFICATE OF CORRECTION

PATENT NO. : 5,932,781
DATED : August 3, 1999
INVENTOR(S) : Takano et al.

It is certified that error appears in the above-identified patent and that said Letters Patent is hereby corrected as shown below:

Column 2, line 29 change "-O-" to ---●---.

Column 3, line 43 change "NO: 4" to --NOS: 4 & 5--.

Column 5, line 18 change "SKLB" to --SK1B--.

Signed and Sealed this

Fifteenth Day of August, 2000

Attest:

Q. TODD DICKINSON

Attesting Officer     *Director of Patents and Trademarks*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 137 amino acids
      (B) TYPE: amino acid
      (C) STRANDEDNESS: Not Relevant
      (D) TOPOLOGY: linear (ii) MOLECULE TYPE: protein (xi) SEQUENCE DESCRIPTION: SEQ ID NO:1:

```
Met Ile Val Arg Asn Leu Glu Glu Ala Arg Gln Thr Asp Arg Leu Val
1               5                   10                  15

Thr Ala Glu Asn Gly Asn Trp Asp Ser Thr Arg Leu Ser Leu Ala Glu
            20                  25                  30

Asp Gly Gly Asn Cys Ser Phe His Ile Thr Arg Ile Phe Glu Gly Thr
        35                  40                  45

Glu Thr His Ile His Tyr Lys His His Phe Glu Ala Val Tyr Cys Ile
    50                  55                  60

Glu Gly Glu Gly Glu Val Glu Thr Leu Ala Asp Gly Lys Ile Trp Pro
65                  70                  75                  80

Ile Lys Pro Gly Asp Ile Tyr Ile Leu Asp Gln His Asp Glu His Leu
                85                  90                  95

Leu Arg Ala Ser Lys Thr Met His Leu Ala Cys Val Phe Thr Pro Gly
            100                 105                 110

Leu Thr Gly Asn Glu Val His Arg Glu Asp Gly Ser Tyr Ala Pro Ala
```

```
                    115                 120                 125
Asp Glu Ala Asp Asp Gln Lys Pro Leu
    130                 135

(2) INFORMATION FOR SEQ ID NO:2:

(i) SEQUENCE CHARACTERISTICS:
        (A) LENGTH: 411 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

ATGATCGTTC GCAATCTCGA AGAAGCGCGC CAGACCGACC GTCTGGTCAC CGCCGAAAAC      60

GGCAACTGGG ACAGCACCCG CCTGTCGCTG GCCGAAGATG GTGGCAACTG CTCCTTCCAC     120

ATCACCCGCA TCTTCGAGGG TACCGAGACC CACATCCACT ACAAGCATCA CTTCGAGGCT     180

GTTTATTGCA TCGAAGGCGA GGGCGAAGTG GAAACCCTGG CCGATGGCAA GATCTGGCCC     240

ATCAAGCCGG TGACATCTA CATCCTCGAC CAGCACGACG AGCACCTGCT GCGCGCCAGC      300

AAGACCATGC ACCTGGCCTG CGTGTTCACG CCGGGCCTGA CCGGCAACGA AGTGCACCGC     360

GAAGACGGTT CCTACGCACC TGCCGACGAA GCCGACGACC AGAAGCCGCT G              411

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:3:

Met Ile Val Arg Asn Leu Glu Glu Ala Arg Gln Thr Asp Arg Leu Val
1               5                   10                  15

Thr Ala Glu Asn Gly Asn Trp Asp Ser Thr Arg Leu Ser Leu
            20                  25                  30

(2) INFORMATION FOR SEQ ID NO:4:

(i) SEQUENCE CHARACTERISTICS:
        (A) LENGTH: 414 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..411

(xi) SEQUENCE DESCRIPTION: SEQ ID NO:4:

ATG ATC GTT CGC AAT CTC GAA GAA GCG CGC CAG ACC GAC CGT CTG GTC        48
Met Ile Val Arg Asn Leu Glu Glu Ala Arg Gln Thr Asp Arg Leu Val
1               5                   10                  15

ACC GCC GAA AAC GGC AAC TGG GAC AGC ACC CGC CTG TCG CTG GCC GAA        96
Thr Ala Glu Asn Gly Asn Trp Asp Ser Thr Arg Leu Ser Leu Ala Glu
            20                  25                  30

GAT GGT GGC AAC TGC TCC TTC CAC ATC ACC CGC ATC TTC GAG GGT ACC       144
Asp Gly Gly Asn Cys Ser Phe His Ile Thr Arg Ile Phe Glu Gly Thr
        35                  40                  45
```

```
GAG ACC CAC ATC CAC TAC AAG CAT CAC TTC GAG GCT GTT TAT TGC ATC        192
Glu Thr His Ile His Tyr Lys His His Phe Glu Ala Val Tyr Cys Ile
    50                  55                  60

GAA GGC GAG GGC GAA GTG GAA ACC CTG GCC GAT GGC AAG ATC TGG CCC        240
Glu Gly Glu Gly Glu Val Glu Thr Leu Ala Asp Gly Lys Ile Trp Pro
65                  70                  75                  80

ATC AAG CCG GGT GAC ATC TAC ATC CTC GAC CAG CAC GAC GAG CAC CTG        288
Ile Lys Pro Gly Asp Ile Tyr Ile Leu Asp Gln His Asp Glu His Leu
                85                  90                  95

CTG CGC GCC AGC AAG ACC ATG CAC CTG GCC TGC GTG TTC ACG CCG GGC        336
Leu Arg Ala Ser Lys Thr Met His Leu Ala Cys Val Phe Thr Pro Gly
                100                 105                 110

CTG ACC GGC AAC GAA GTG CAC CGC GAA GAC GGT TCC TAC GCA CCT GCC        384
Leu Thr Gly Asn Glu Val His Arg Glu Asp Gly Ser Tyr Ala Pro Ala
            115                 120                 125

GAC GAA GCC GAC GAC CAG AAG CCG CTG TAA                                414
Asp Glu Ala Asp Asp Gln Lys Pro Leu
130                 135
```

(2) INFORMATION FOR SEQ ID NO:5:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ile Val Arg Asn Leu Glu Glu Ala Arg Gln Thr Asp Arg Leu Val
1                   5                   10                  15

Thr Ala Glu Asn Gly Asn Trp Asp Ser Thr Arg Leu Ser Leu Ala Glu
                20                  25                  30

Asp Gly Gly Asn Cys Ser Phe His Ile Thr Arg Ile Phe Glu Gly Thr
                35                  40                  45

Glu Thr His Ile His Tyr Lys His His Phe Glu Ala Val Tyr Cys Ile
    50                  55                  60

Glu Gly Glu Gly Glu Val Glu Thr Leu Ala Asp Gly Lys Ile Trp Pro
65                  70                  75                  80

Ile Lys Pro Gly Asp Ile Tyr Ile Leu Asp Gln His Asp Glu His Leu
                85                  90                  95

Leu Arg Ala Ser Lys Thr Met His Leu Ala Cys Val Phe Thr Pro Gly
                100                 105                 110

Leu Thr Gly Asn Glu Val His Arg Glu Asp Gly Ser Tyr Ala Pro Ala
            115                 120                 125

Asp Glu Ala Asp Asp Gln Lys Pro Leu
130                 135
```